United States Patent [19]

Elmaleh et al.

[11] Patent Number: 5,493,026

[45] Date of Patent: Feb. 20, 1996

[54] SUBSTITUTED 2-CARBOXYALKYL-3-(FLUOROPHENYL)-8-(3-HALOPROPEN-2-YL) NORTROPANES AND THEIR USE AS IMAGING FOR AGENTS FOR NEURODEGENERATIVE DISORDERS

[75] Inventors: David R. Elmaleh; Bertha K. Madras; Robert N. Hanson, all of Newton; Peter Meltzer, Lexington, all of Mass.

[73] Assignees: Organix, Inc., Woburn; The General Hospital Corporation, Boston; President and Fellows of Harvard College, Cambridge; Northeastern University, Boston, all of Mass.

[21] Appl. No.: 142,584

[22] Filed: Oct. 25, 1993

[51] Int. Cl.[6] .................................................. C07D 451/02
[52] U.S. Cl. ................................................................. 346/132
[58] Field of Search ........................... 546/132; 514/304; 424/1.85, 1.89

[56] References Cited

U.S. PATENT DOCUMENTS

| | | | |
|---|---|---|---|
| 3,452,029 | 6/1969 | Childress et al. | 260/292 |
| 5,128,118 | 7/1992 | Carroll et al. | 424/1.1 |
| 5,268,480 | 12/1993 | Kozikowski | 546/23 |
| 5,310,912 | 5/1994 | Neumeyer et al. | 546/132 |

OTHER PUBLICATIONS

Van der Zee et al., "A comparison of the inhibitory effects of aromatic substituted benzhydryl . . . into synaptosomal preparations of the rat brain", *Neuropharmacology*, 17(7), 483–90, 1978.

Abstract #275, "Radioiodinated 2beta–Carbomethoxy–3beta (4–Chlorophenyl)-8-(3E- and 3Z-Iodopropen-2-yl) Nortropanes", Journal of Nuclear Medicine 33:890, 1992.

Carroll et al., "Synthesis, Ligand Binding, QSAR, and CoMFA Study . . . ", Journal of Medicinal Chemistry 34:2719–2725, 1991.

Madras et al., "N–Modified Fluorophenyltropane Analogs . . . ", Pharmacology, Biochemistry & Behavior 35:949–953, 1990.

Milius et al., "Synthesis and Receptor Binding of N–Substituted Tropane Derivatives . . . ", Journal of Medicinal Chemistry 34:1728–1731, 1991.

Boja et al. "New, Potent Cocaine Analogs: Ligand Binding and Transport Studies in Rat Striatum" European J. of Pharmacology, 184:329–332 (1990).

Brownell et al. "Use of [C–11] 2β–Carbomethoxy–3B–4–Fluorophenyl Tropane ([C–11 CFT) in Studying Dopamine Fiber Loss in a Primate Model of Parkinsonism" J. Nuclear Med. Abs., 33:946 (1992), Ab#512.

Canfield et al. "Autoradiographic Localization of Cocaine Binding Sites by [$^3$H]CFT ([$^3$H]WIN 35,428) in the Monkey Brain" Synapse, 6:189–195 (1990).

Carroll et al. "Probes for the Cocaine Receptor. Potentially Irreversible Ligands for the Dopamine Transporter" J. Med. Chem., 35:1813–1817 (1992).

Carroll et al. "Cocaine Receptor: Biochemical Characterization and Structure–Activity Relationships of Cocaine Analogues at the Dopamine Transporter" J. Med. Chem., 35:969–981 (1992).

Carroll et al. "Synthesis, Ligand Binding, OSAR, and CoMFA Study of 3β–(p-Substituted phenyl)tropane–2β–carboxylic Acid Methyl Esters" J. Med. Chem., 34:2719–2725 (1991).

Elmaleh et al. "PET Imaging Probes for the Cocaine Receptors: A Validation Study in a Nonhuman Primate Model" J. Nuclear Med. Abs., 33:946 (1992), Ab #511.

(List continued on next page.)

*Primary Examiner*—Shean Wu
*Assistant Examiner*—Lara E. Chapman
*Attorney, Agent, or Firm*—Fish & Richardson

[57] ABSTRACT

Disclosed are certain cocaine analogs useful for imaging of cocaine receptors and dopamine receptors. Also disclosed are analogs useful for imaging diagnostics for Parkinson's disease.

14 Claims, 3 Drawing Sheets

OTHER PUBLICATIONS

Goodman et al. "Radioiodinated 2β-Carbomethoxy-3β-(4-Chlorophenyl)-8-(3E-and 3Z-Iodopropen-2-YL)Nortropanes: Synthesis of Potential Radioligands for Mapping Cocaine Receptor..." J. Nuclear Med. Abs., 33:890 (1992), Ab #275.

Kaufman et al. "Severe Depletion of Cocaine Recognition Sites Associated With the Dopamine Transporter in Parkinson's–Diseased Striatum" Synapse, 9:43–49 (1991).

Madras "[11]C–WIN 35,428 for Detecting Dopamine Depletion in Mild Parkinson's Disease" Annals of Neuro., 35:376–379 (1994).

Madras et al. "N–Modified Fluorophenyltropane Analogs of Cocaine With High Affinity for Cocaine Receptors" Pharmacol. Biochem. & Behav., 35:949–953 (1990).

Meltzer et al. "Substituted 3–Phenyltropane Analogs of Cocaine: Synthesis, Inhibition of Binding at Cocaine Recognition Sites, and Positron Emission Tomography Imaging" J. Med. Chem., 36:855–862 (1993).

Milius et al. "Synthesis and Receptor Binding of N–Substituted Tropane Derivatives. High–Affinity Ligands for the Cocaine Receptor" J. Med. Chem., 34:1728–1731 (1991).

Reith et al. "Radiolabeling of Dopamine Uptake Sites in Mouse Striatum: Comparison of Binding Sites for Cocaine, Mazindol, and GBR 12935" Arch. of Pharmacol., 345:309–318 (1992).

Reith et al. "Structural Requirements for Cocaine Congeners to Interact with Dopamine and Serotonin Uptake Sites in Mouse Brain and to Induce Sterotyped Behavior" Biochem. Pharmacol., 35:1123–1129 (1986).

Isacson, "Clinical and Preclinical PET Correlates of Parkinsonism with [11]C–WIN 35,428" Annals of Neurology, 35:377–378 (1994).

Meyer et al. "Intravenously Administered Dopamine Transporter Site Radioligand Is Not Significantly Retained in Mouse Substantia Nigra or Other Sites Outside of Basal Ganglia" Annals of Neurology, 35:378–379 (1994).

SUBSTITUTED 2-CARBOXYALKYL-3-(FLUOROPHENYL)-8-(3-HALOPROPEN-2-YL) NORTROPANES AND THEIR USE AS IMAGING FOR AGENTS FOR NEURODEGENERATIVE DISORDERS

STATEMENT OF FEDERALLY SPONSORED RESEARCH

This invention was supported by NIH Grant Numbers DA06303 and DA00499, and the government has certain rights in this invention.

BACKGROUND OF THE INVENTION

The invention relates to substituted nortropanes and their use to image: a) dopamine-transporter-containing neurons, particularly in connection with diagnosis and study of certain neurodegenerative disorders; and b) cocaine receptors.

There is a need for diagnostic agents and markers of neurogenerative disorders such as Parkinson's disease. For example, exclusion at an early stage of Parkinson's disease as the cause of symptoms may be useful information in diagnosing other conditions. Moreover, early diagnosis of Parkinson's disease can facilitate the introduction of putative prophylactic drug therapy (e.g., deprenyl) prior to the onset of more severe symptoms. See, Kaufman and Madras (1991) Synapse 9:43–49. Detection of nerve cell depletion in the presymptomatic phase in an animal model of Parkinson's disease would also be useful, e.g., when using the model to evaluate therapies for Parkinson's disease. See, Hantraye et al. (1992) Neuro Reports 3:265–268; and Hahtraye et al. (1992) Soc. Neurosci. Abstra. 18:935.

There is a particular need for diagnostic agents and markers of neurogenerative disorders that selectively target a dopamine transporting protein (the dopamine transporter) in preference to another protein known as the serotonin transporter. In normal brain tissue, the dopamine:serotonin transporter density ratio is approximately 10:1. In certain neurodegenerative disorders, such as Parkinson's disease, nerve cells that produce dopamine (and on which the dopamine transporter is located) undergo severe depletion, while serotonin nerve cells are less affected. The dopamine::serotonin transporter ratio can fall to 50% in Parkinson's disease.

Various substances (particularly cocaine and cocaine congeners) are potent inhibitors of dopamine transport in the striatum of the brain because they bind to the dopamine transporter. The more strongly these substances block dopamine transport, the more strongly they bind to sites on the dopamine transporter which have been labeled by [$^3$H] cocaine or by a compound known as [$^3$H] CFT (also known as [$^3$H]WIN 35,428).[1] See, Madras et al., (1989) J. Pharmacol. Exp. Ther. 251:131–141; and Madras et al. (1989) Mol. Pharmacol. 36:518–524.

[1] 2-carboxymethyl-3-(4-fluorophenyl)tropane.

CFT (WIN 35,428) and similar substances exhibit markedly decreased binding in the Parkinson's diseased brain. See, Madras et al. Soc. Neurosci. Abst. 16:14, 1990; and Kaufman and Madras (1991) Synapse 9:43–49. The hope that these compounds might be Parkinson's markers is further supported by the parallel between loss of binding and loss of dopamine in the diseased brain (Madras et al. Catechol. Symp. 193, 1992).

Dopamine transporter-binding compounds that have been studied include N-allyl-2 carboxymethyl-3β-fluorophenyl-tropane. See, Madras et al. (1990) Pharmacology, Biochemistry & Behavior 35:949–953; and Milius et al. (1991) J. Med. Chem. 34:1728–1731.

Goodman et al. report (1992) J. Nuclear Med. 33:890) the synthesis of 2-β-carbomethoxy-3-β-(4-chlorophenyl)-8-($^{123}$I-iodopropene-2yl) nortropane. The selectivity of this analog for the dopamine over the serotonin transporter is not discussed.

CFT or WIN 35,428 is approximately 15 times more selective for the dopamine over the serotonin transporter. The 4-chloro analog is 4-fold selective. See Carroll et al., J. Med. Chem. 35:969 (1992); and Meltzer et al., J. Med. Chem. 36:855–862 (1993).

SUMMARY OF THE INVENTION

We have discovered that fluorination of the phenyl substituent of N-haloallyl phenyl nortropanes yields compounds that are unusually effective for several purposes. The 3E and 3Z isomers of 2-β-carbomethoxy-3-β-(4-fluorophenyl)-8-(3-I-iodopropen-2-yl) nortropane are particularly preferred. We have designated this preferred compound Iodoaltropane or IACFT. Most preferably, the compounds according to the invention are labeled with radionuclides of the halogen series, such as $^{123}$I or $^{125}$I.

The special properties of the claimed compounds are best understood with the following background. Cocaine recognition sites are localized on the dopamine transporter, which itself is localized on dopamine nerve terminals. Drugs that bind to these sites therefore have potential uses which include: (i) imaging probes for neurodegenerative disorders; and (ii) imaging probes for dopamine transporter/cocaine binding sites.

Because of the unique anatomical location of the cocaine recognition sites, a high affinity probe for imaging of these sites in vivo in the brain can be carried out using PET or SPECT imaging. Such imaging is useful for diagnosing or monitoring Parkinson's disease, a neurological disorder characterized by the degeneration of dopamine nerve terminals or by aging.

Accordingly, one aspect of the invention features a compound of formula:

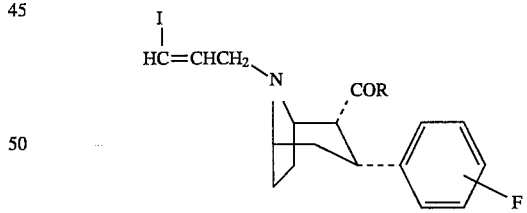

wherein the following condition is imposed on that formula:

R is —CH$_3$, —CH$_2$CH$_3$ (α configuration; β configuration or both), —CH(CH$_3$)$_2$, —(CH$_2$)$_n$CH$_3$, —(CH$_2$)$_n$C$_6$H$_4$X, —C$_6$H$_4$X, —C$_6$H$_5$, —OCH$_3$, —OCH$_3$CH$_2$, —OCH(CH$_3$)$_2$, —OC$_6$H$_5$, —OC$_6$H$_4$X, —O(CH$_2$)$_n$C$_6$H$_4$X, or —O(CH$_2$)$_n$CH$_3$; wherein X is —Br, —Cl, —I , —F, —OH, —OCH$_3$, —CF$_3$, —NO$_2$ —NH$_2$, —CN, —NHCOCH$_3$, —N(CH$_3$)$_2$, —(CH$_2$)$_n$ CH$_3$, CHOCH$_3$, or —C(CH$_3$)$_3$ and n is between 0 and 6 inclusive A second aspect of the invention features the same formula, except that the substituent on the N-allyl group can generally be any halogen, preferably —I or —F.

In a third aspect, the invention features a method of detecting parkinsonism in a human patient, involving administering to the patient a detectably labelled compound of the invention and detecting its binding to CNS tissue, e.g., by quantifying dopamine terminals with that compound (e.g., using positron emission tomography (PET) or single-photon emission computed tomography (SPECT)).

In a fourth aspect, the compound is used to monitor cocaine binding sites of the CNS (e.g. to determine site occupancy by potential cocaine therapeutics).

Such compounds also may be useful in treatment of neurodegenerative disorders or cocaine abuse.

Preferred compounds according to the invention are characterized as follows: a) the 2 substituent is in the β position; b) the 3 substituent is in the β position; c) R is —O—CH$_3$; the 8 substituent is either the E isomer or the Z isomer. More preferably the halo substituent on the N-allyl moiety is —I or —Br (particularly a radionuclide of —I or —Br); $^{18}$F provides also a useful label. Most preferably, the compound is Iodoaltropane: 2-β-carbomethoxy-3-β-(4-fluorophenyl)-8-(3E-iodopropen-2-yl) nortropane.

Also in preferred embodiments, the compound contains a radioactive label (particularly a gamma or position emitter such as $^{123}$I, $^{125}$I $^{18}$F or $^{11}$C $^{123}$I is particularly preferred) or a $^{18}$F fluoro label as part of the 3-halopropen- 2-yl substituent.

Therapeutic compositions according to the invention comprise a compound as described above formulated in a pharmaceutically acceptable carrier. Such compositions can be used to selectively image cocaine binding regions of the central nervous system of a human patient by administering detectably labelled compound to the central nervous system and detecting the binding of that compound to CNS tissue. The compositions can also be used to detect parkinsonism in a human patient by administering detectably labelled compound to the patient and detecting the binding of the compound to CNS tissue (e.g., by position emission tomography (PET) or by single-photon emission computed tomography (SPECT)). Such a compound also may be useful in treatment of neurodegenerative disorders characterized by dopamine deficits or cocaine abuse.

DETAILED DESCRIPTION OF THE DRAWINGS

I. Compound Characterization

Target compounds are prepared as the free bases or salts, e.g., the naphthalene-1,5-disulfonate, tartrate, or hydrochloride salts. For example, these compounds are prepared from the corresponding Z or E iodo-tri-n-butylstannylallyl precursors. See Example 1, below.

Figure 3:
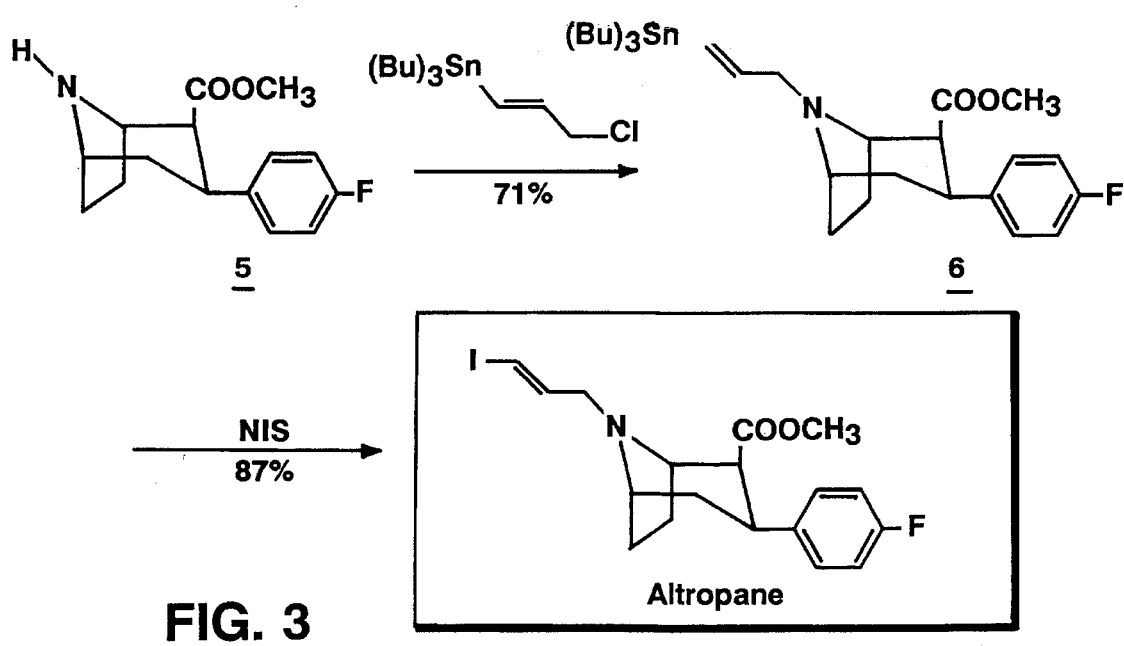
FIG. 3 is a diagram of the synthesis of Iodoaltropane.

Compounds can be radiolabeled at any of a number of positions. For example, a radionuclide of the halogen series may be used in the haloallyl moiety. Alternatively, a radionuclide can be included in the —R moiety defined above. Radiolabeled iodoallyl compounds may be prepared by reacting the iodoallyl Sn precursor (see FIG. 3) with a radioiodide (provided, e.g., as NaI) under oxidative conditions (e.g., H$_2$O$_2$ or benzoyl peroxide).

Characterization of the compounds is carried out using standard methods of high field NMR spectra as well as IR, MS and optical rotation. Elemental analysis, TLC and/or HPLC is used as a measure of purity. A purity of >98% is preferred before biological evaluation of these compounds is undertaken.

II. Binding Assays for Candidate Compounds

To evaluate the selectivity of N-haloallyl nortropane derivatives for the dopamine transporter, compounds are screened in radioreceptor assays using both [$^3$H]CFT and [$^3$H]citalopram as probes for the dopamine and serotonin receptors, respectively. The relative affinities of a compound for either site establishes whether it binds selectively to the dopamine transporter or non-selectively to the serotonin transporter as well. Assays are carried out as follows.

Competition studies to determine the potency of a compound for inhibiting specifically bound [$^3$H]CFT in monkey caudate-putamen membranes are conducted using 0.3–10 nM [$^3$H]CFT and the primate brain tissue preferably caudate-putamen. The methods are described by Madras et al. (1989) Mol. Pharmacol. 36:518–524. Unlabeled (-)-cocaine (30 µM) serves as the baseline drug to detect non-specific binding. Incubation proceeds at 4° C. for 60 min, and the assay is terminated by vacuum filtration over glass fiber filters (Whatman GF/B). The filters are monitored for radioactivity by liquid scintillation spectrometry at 50% counting efficiency. All assays are performed in triplicate, and each experiment is repeated at least twice using tissue from different brains.

To assay binding of the analog to the serotonin transporter, analogs are tested for their ability to compete with labeled [$^3$H]citalopram, a high affinity and selective ligand for serotonin transporter sites (D'Amato et al., J. Pharmacol. Exp. Ther. 242:364–371, 1987). Radioreceptor assays are conducted using tissues prepared as described above. Analogs are incubated with buffer (50 mMTris HCl; 100 mM NaCl), [$^3$H]citalopram (1 nM), and tissue (1 mg/ml wet tissue weight), incubated 2 h at 4° C., and the incubation terminated by rapid filtration. Non-specific binding is monitored with fluoxetine (1 µM).

Using such an approach, the compounds according to the invention may be tested for their ability to inhibit the binding of [$^3$H]CFT to primate caudate-putamen. Inhibition by (-)-cocaine and CFT may be used as reference points.

III. SPECT or PET IMAGING

Autoradiographic distribution of the compounds are conducted according to in vitro techniques (Kaufman et al. (1991) Synapse 9:177–187) or ex vivo techniques (Kaufman and Madras (1992) Synapse 12:99–111).

The cocaine analogs described herein provide useful SPECT or PET imaging probes. Brain imaging has at least two applications: to monitor the dopamine transporter (dopamine nerve terminals) in neurodegenerative disorders and cocaine abuse; and to evaluate the time course of accumulation of a candidate drug therapy in the brain targeting the dopamine transporter, as well as the duration of receptor occupancy. Such compounds may be useful for cocaine abuse or other neuro-psychiatric disorders.

Cocaine analogs of high affinity are most useful as SPECT (or PET) imaging probes because they display a low level of non-specific binding, and they accumulate in dopamine regions of brain. High affinity analogs are preferable because dopamine may compete effectively with trace doses of low affinity analogs in vivo. By these standards, Iodoaltropane is a high affinity ligand.

SPECT or PET imaging may be carried out using any appropriate apparatus. Imaging is carried out on conscious human subjects using standard imaging (see, e.g., *Medicine, Scientific American, Inc.,* ed. Rubenstein and Federman, 1988; Jaszczak and Coleman, *Invest. Radiol.* 20:897, 1985; Coleman et al., *Invest. Radiol.* 21:1, 1986); preferably SPECT imaging employs gamma-emitting derivatives of the analogs described herein (e.g., analogs labelled with $^{123}$I).

IV. Analytical Considerations

All target compounds are prepared either as free bases or as suitable pharmacologically active salts such as hydrochloride, tartrate, naphthalene-1,5-disulfonate salts or the like. All target compounds are characterized and their purity analyzed prior to any biological evaluation. High field NMR spectra are measured as well as IR, MS and optical rotation for all test compounds. Elemental analysis, TLC and/or HPLC are used as a measure of purity. A purity of >98% is required before any biological evaluation of these compounds is undertaken.

The following specific examples illustrate but does not limit the invention.

EXAMPLE 1: GENERAL PROCEDURES FOR THE PREPARATION OF IODOALTROPANE

Tributyltinallyl Alcohol

Propargyl alcohol (5.5. mL, 9.4 mmol) was added dropwise to a mixture of tributyltin hydride (35 mL, 13 mmol) and azobis (isobutyronitrile) (AIBN) (1.6 g, 0.97 mmol) at 80° C. The reaction mixture was heated at 80° C. for 2 h. The reaction mixture was chromatographed over silica gel (5% EtOAc/hexane) to afford the E-isomer 16.68 g (51%) and the Z-isomer (23%) as a clear oil.

Tributyltinallyl Chloride

Tributyltinallyl alcohol (12.8 g, 3.7 mmol), triphenylphosphine (9.7 g, 3.7 mmol) and CCl$_4$ (100 mL) were combined and heated at reflux for 16 h. Excess CCl$_4$ was removed and the residue was chromatographed over silica gel (hexane) to afford 10.78 g (80%) of tributyltin allyl chloride as a clear oil.

Methyl-3β-(p-fluorophenyl)-N-tributyltinallyl-1αH-, 5βH-nortropane- 2β-carboxylate Methyl-3β-(p-fluorophenyl)-1αH,5αH-nortropane-2β-carboxylate (102 g, 0.39 mmol), (see Meltzer et al., *J. Med. Chem.* 36:855 (1993)) tributyltin allyl chloride (143 mg, 0.39 mmol), KF-celite (50%, 226 mg, 1.9 mmol) and CH$_3$CN (10 mL) were combined and heated at 70° C. for 17 h. The reaction mixture was diluted with 40 mL of ether and filtered through a celite pad. The filtrate was concentrated to dryness. The residue was chromatographed over silica gel (2% Et$_3$N/hexane) to afford 163 mg (71%) of methyl-3β-)p-fluorophenyl)-N-tributyltinallyl- 1αH-,5αH-nortropane-2β-carboxylate.

Methyl-3β-(p-fluorophenyl)-N-iodoallyl-1αH-,5αH-nortropane-2β-carboxylate

Methyl-3β-(p-fluorophenyl)-N-tributyltinallyl-1αH-,5αH-nortropane-2β-carboxylate (161 mg, 0.27 mmol) in THF (10 mL) was degassed by bubbling N$_2$ through for 5 min. NIS (61.8 mg, 0.275 mmol) was added and stirred at room temperature for 15 min. THF was removed and the residue was chromatographed over silica gel (2% Et$_3$N/hexane) to afford 102 mg (87%) of methyl-3β(p-fluorophenyl)-N-iodoallyl-1αH- ,5αH-nortropane-2β-carboxylate as a white solid: mp 112°– 114° C.

Thus, propargyl alcohol was treated with tributyl tin hydride in the presence of azobis (isobutyronitrile) to obtain, after column chromatography over silica gel, the separated E and Z isomers of 3-tributyltin allyl alcohol. Each of the alcohols was then reacted with triphenylphosgene and carbon tetrachloride to obtain the requisite E and Z isomers of 3-tributyltin allyl chloride respectively.

Reaction of each of the 3-tributyltin allyl chlorides with methyl-3β-(p-fluorophenyl)nortropane-2β-carboxylate (see Meltzer et al., *J. Med. Chem.* 36:855 (1993) for the synthesis of this compound) in the presence of KF-celite gave the desired methyl-3β-(p-fluorophenyl)-N-(3-tributyltin allyl)-nortropane-2β-carboxylate in 71% yield after column chromatography. Conversion of this compound to the iodide was effected with N-iodosuccinimide (NIS) in THF to obtain methyl-3β-(p-fluorophenyl)-N-(3-iodo allyl)-nortropane-2β-carboxylate (Iodoaltropane) in 87% yield.

EXAMPLE 2: PREPARATION OF BROMOALTROPANE

The 2-β-carbomethoxy-3-β-(4-fluorophenyl)-8-(3-bromopropen- 2-yl) analog ("Bromoaltropane") is prepared generally as described above using N-bromosuccinimide (NBS) in place of NIS.

EXAMPLE 3: FLUORINATION

The fluoroallyl compounds may be prepared by reacting a corresponding haloallyl Sn compound with Xe$_2$F$_2$, acetylhypofluroide, or F$_2$.

EXAMPLE 4

Iodoaltropane was compared to CFT as well as to another candidate iodinated dopamine transporter probes known as RTI-55,[2] using the above-described radioreceptor 2 binding techniques on monkey striation homogenate. The results are as follows.

[2] 2-carboxymethyl-3-(4-iodophenyl)tropane.

Figure 1:
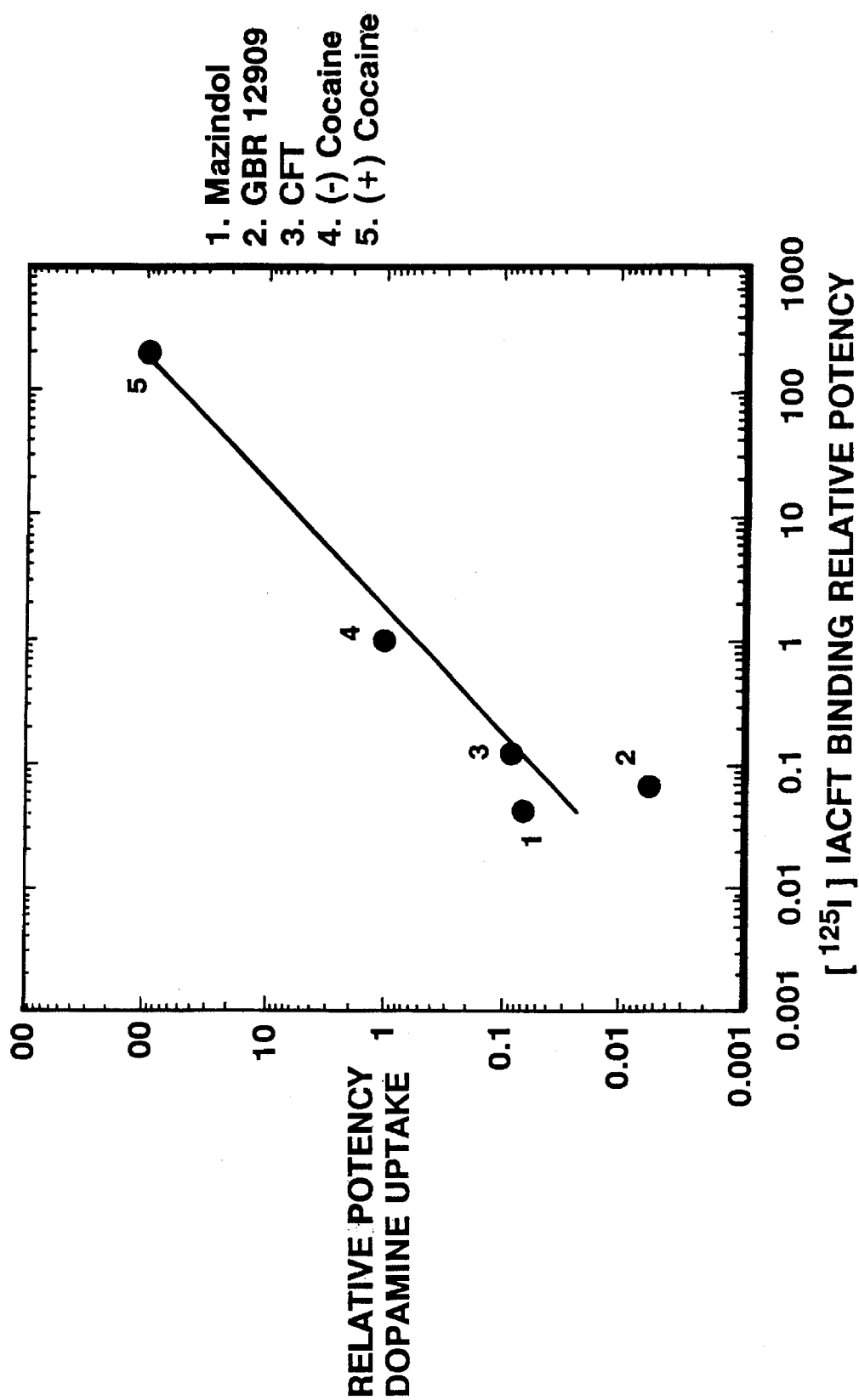
FIG. 1 is a graph depicting association of $^{125}$I iodoaltropane with the dopamine transporter. The pharmacological specificity of [$^{125}$I] iodoaltropane labeled sites (primate striatum) and the dopamine transporter sites (rodent striatum) are closely associated.
Figure 2A:
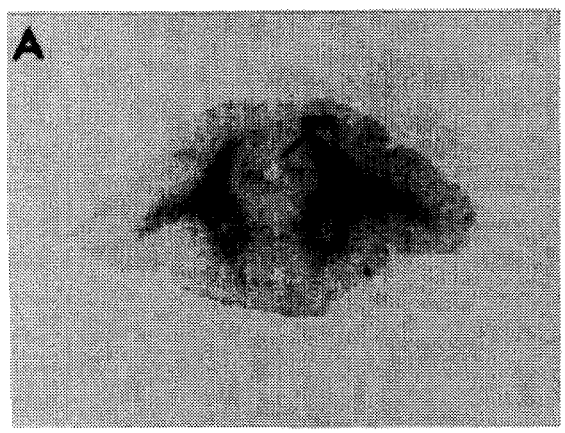
FIGS. 2A–2F are photographs depicting the distribution of $^{125}$I Iodoaltropane in a primate brain, indicating a close match between that distribution and the distribution of dopamine.
Figure 2B:
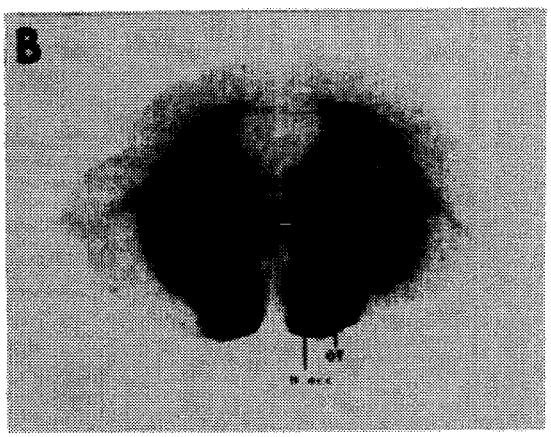
Figure 2C:
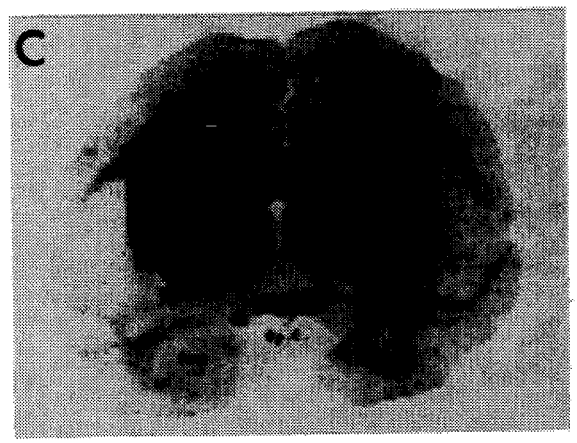
Figure 2D:
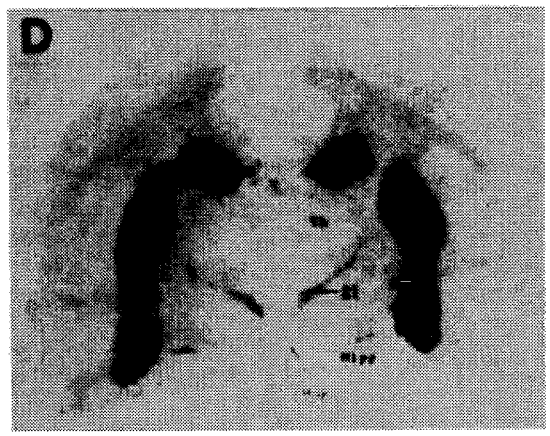
Figure 2E:
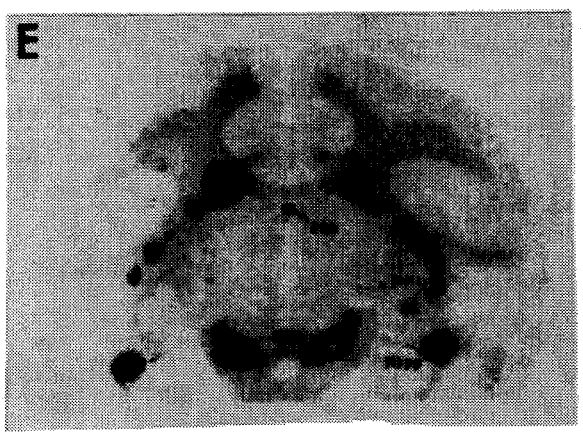
Figure 2F:
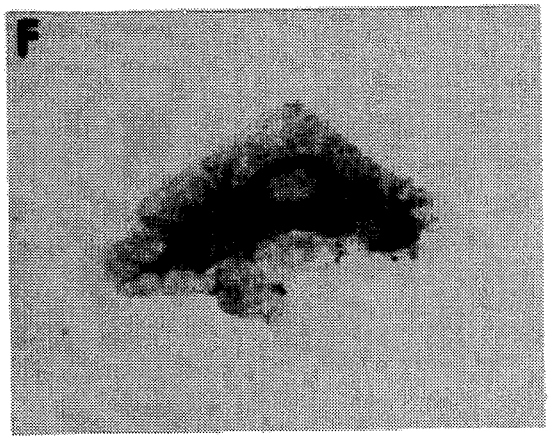

1. Iodoaltropane is more selective for the dopamine transporter and possesses higher affinity than CFT (Table 1).
2. Iodoaltropane is more selective than RTI-55, which has a high affinity but low selectivity for the dopamine transporter (Table 1).
3. [$^{125}$I]Iodoaltropane labels the dopamine transporter in primate striatum (see FIG. 1).
4. [$^{125}$I]Iodoaltropane distributes primarily to dopamine-rich brain regions in primate brain (FIGS. 2A–2F) and its binding is characterized by low levels of nonspecific binding.

TABLE 1

Affinity of Iodoaltropane for the dopamine and serotonin transporter

| | Dopamine trans. | Serotonin trans. | Selectivity |
|---|---|---|---|
| Iodoaltropane | 6.62 ± 0.78 | 182 ± 46 | 28 |
| CFT | 12.9 ± 1.10 | 160 ± 20 | 15 |
| RTI-55 | 1.08 ± 0.06 | 2.53 ± 0.02 | 2 |
| Bromoaltropane | 10.8 | 212 | 20 |

What is claimed is:

1. A compound of formula:

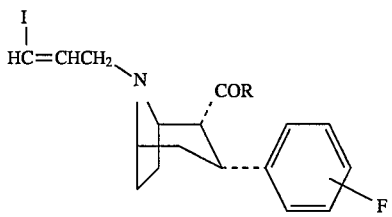

wherein the following conditions are imposed on that formula:

R is —CH₃, —CH₂CH₃, —CH(CH₃)₂, —(CH₂)ₙCH₃, —(CH₂)ₙC₆H₄X, —C₆H₄X, —C₆H₅, —OCH₃, —OCH₃CH₂, —OCH(CH₃)₂, —OC₆H₅, —OC₆H₄X, —O(CH₂)ₙC₆H₄X, or —O(CH₂)ₙCH₃; wherein X is —Br, —Cl, —I, —F, —OH, —OCH₃, —CF₃, —NO₂ —NH₂, —CN, —NHCOCH₃, —N(CH₃)₂, (CH₂)ₙCH₃, CHOCH₃, or —C(CH₃)₃, and n is between 0 and 6 inclusive.

2. A compound of formula:

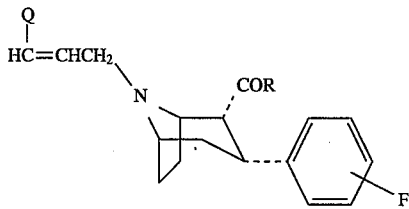

wherein the following conditions are imposed on that formula:

a) R is —CH₃, —CH₂CH₃, —CH (CH₃)₂, (CH₂)ₙCH₃, —(CH₂)ₙC₆H₄X, —C₆H₄X, —C₆H₅, —OCH₃, —OCH₃CH₂, —OCH(CH₃)₂, —OC₆H₅, —OC₆H₄X, —O(CH₂)ₙC₆H₄X, or —O(CH₂)ₙCH₃; wherein X is —Br, —Cl, —I, —F, —OH, —OCH₃, —CF₃, —NO₂ —NH₂, —CN, —NHCOCH₃, —N(CH₃)₂, —(CH₂)ₙCH₃, CHOCH₃, or —C(CH₃)₃, and n is between 0 and 6 inclusive; and b) where —Q is a halogen.

3. The compound of claim 1 or claim 2 having formula A or B:

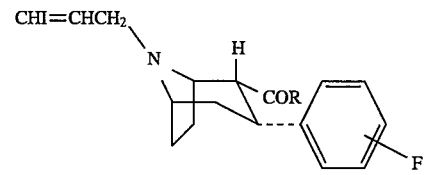

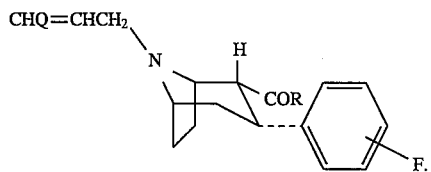

4. The compound of claim 1 or claim 2 having formula C or D:

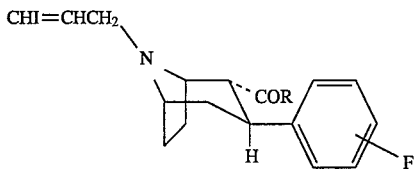

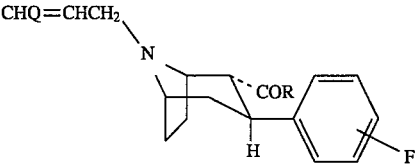

5. The compound of claim 1 or claim 2 in which R is —O—CH₃.

6. The compound of claim 1 having the formula:

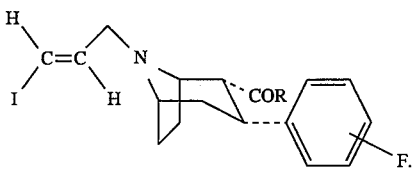

7. The compound of claim 1 having the formula:

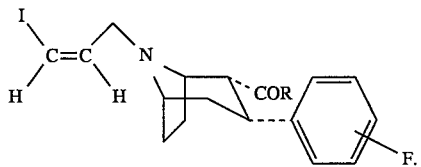

8. The compound of claim I or claim 2 in which said compound is 2-β-carbomethoxy-3-β-(4-fluorophenyl)-8-(3-iodopropen- 2-yl) nortropane.

9. The compound of claim 1 or claim 2 in which at least one atom of said compound is a radioactive isotopic label.

10. The compound of claim 9 in which said label is a gamma or positron emitter.

11. The compound of claim 10 in which said label is selected from the group consisting of 125I, ¹²³I ¹⁸F and ¹¹C.

12. The compound of claim 10 in which said label is ¹²³I.

13. The compound of claim 2 where Q is —Br.

14. The compound of claim 2 having the formula:

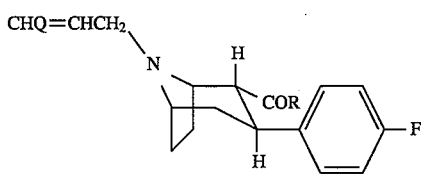

* * * * *

UNITED STATES PATENT AND TRADEMARK OFFICE
CERTIFICATE OF CORRECTION

PATENT NO. : 5,493,026

DATED : February 20, 1996

INVENTOR(S) : David R. Elmaleh et al.

It is certified that error appears in the above-identified patent and that said Letters Patent is hereby corrected as shown below:

Title page, item
In the Abstract, first line, "Disclosed are certain cocaine analogs" should be --Novel substituted 2-carboxyalkyl-3-(fluorophenyl)-8-(3-halopropeny-2-yl nortropanes are-- (as Col. 1, line 35, "Hahtraye" should be --Hantraye--;
       line 58, please move the footnote to the bottom of the page.

Col. 3, line 24, after "C" insert --;--.

Col. 5, line 48, "5βH" should be --5αH--

Col. 6, line 44, move the footnote to the bottom of the page and delete "2" (first occurrence).

Col. 7, claim 1, line 19, "(CH$_2$)" should be "-(CH$_2$)".

Col. 8, claim 8, line 36, "claim I or claim 2" should be --claim 1--;
                line 38, "nortropane" should be --norptropane--.

UNITED STATES PATENT AND TRADEMARK OFFICE
CERTIFICATE OF CORRECTION

PATENT NO. : 5,493,026
DATED : February 20, 1996
INVENTOR(S) : David R. Elmaleh, et. al.

It is certified that error appears in the above-indentified patent and that said Letters Patent is hereby corrected as shown below:

Col. 8, claim 11, line 45, "125I" should be $125_I$--.

Signed and Sealed this

Fourteenth Day of January, 1997

BRUCE LEHMAN

Attest:

Attesting Officer

Commissioner of Patents and Trademarks